United States Patent [19]
Devictor et al.

[11] Patent Number: 5,420,248
[45] Date of Patent: May 30, 1995

[54] UNPIGMENTED FISH SKIN, PARTICULARLY FROM FLAT FISH, AS A NOVEL INDUSTRIAL SOURCE OF COLLAGEN, EXTRACTION METHOD, COLLAGEN AND BIOMATERIAL THEREBY OBTAINED

[75] Inventors: Pierre Devictor, Lyons; Roland Allard, St.Genis-Laval; Eric Perrier, Vienne; Alain Huc, Sainte Foy-les-Lyon, all of France

[73] Assignee: Coletica, Lyons, France

[21] Appl. No.: 170,353

[22] PCT Filed: Jul. 2, 1992

[86] PCT No.: PCT/FR92/00621
§ 371 Date: Jan. 4, 1994
§ 102(e) Date: Jan. 4, 1994

[87] PCT Pub. No.: WO93/01241
PCT Pub. Date: Jan. 21, 1993

[30] Foreign Application Priority Data
Jul. 4, 1991 [FR] France ............................ 91 08400

[51] Int. Cl.⁶ ................... C07K 14/78; C07K 1/14; A61K 38/39; A61K 7/00
[52] U.S. Cl. ................... 530/356; 530/857; 602/42; 602/43; 602/48; 602/50; 106/124; 106/125; 424/443; 424/444; 424/445
[58] Field of Search ............ 530/356, 857; 602/42, 602/43, 48, 50; 106/124, 125; 424/443, 444, 445, 572, 574

[56] References Cited
U.S. PATENT DOCUMENTS
4,511,653 4/1985 Play et al. ..................... 435/68.1
4,621,631 11/1986 Pâques et al. ..................... 424/443
5,093,474 3/1992 Grossman et al. ................. 530/355
5,106,949 4/1992 Kemp et al. ..................... 530/356
5,162,506 11/1992 Hadden ........................... 530/412

FOREIGN PATENT DOCUMENTS
582543 12/1924 France .
582544 12/1924 France .
647030 11/1928 France .
736769 3/1943 Germany .
229190 10/1943 Switzerland .

OTHER PUBLICATIONS

The Aquarium Encyclopedia by Günther Sterba, p. 453 Pleuronectiformes.
*Chemical Abstracts*, vol. 107, No. 17, Oct. 26, 1987, Abstract No. 150796f, p. 382 (abstract of JP-A-62083849).
S. C. Gantayat et al., "Collagen Content of Skin of Fresh Water Teleost," *Indian Journal of Experimental Biology*, vol. 18, No. 7, Jul. 1, 1980, pp. 733–735.

*Primary Examiner*—Michael G. Wityshyn
*Assistant Examiner*—Nancy J. Degen
*Attorney, Agent, or Firm*—Millen, White, Zelano & Branigan

[57] ABSTRACT

The present invention relates to the use of unpigmented skin from flat fish as novel industrial source of collagen. As unpigmented skin, the ventral skin is used in particular, from sole, dab, turbot, brill. Native acid-soluble collagen is advantageously extracted and separated by precipitation from the supernatant. The invention makes it possible to improve the collagen yield at reduced cost while preserving the native properties of the protein, and in a reproducible manner.

18 Claims, No Drawings

UNPIGMENTED FISH SKIN, PARTICULARLY FROM FLAT FISH, AS A NOVEL INDUSTRIAL SOURCE OF COLLAGEN, EXTRACTION METHOD, COLLAGEN AND BIOMATERIAL THEREBY OBTAINED

The present invention relates essentially to the use of unpigmented fish skin, particularly from fiat fish, as novel industrial source of collagen, to a method for extracting the collagen, as well as to the collagen and biomaterial thereby obtained.

BACKGROUND OF THE INVENTION

Collagen, as a protein for strengthening the connective tissues of human beings, finds ever expanding applications in the cosmetic and pharmaceutical fields.

The main properties are as follows:
good mechanical properties,
action on cell development, hence on tissue regeneration,
hemostatic power,
excellent biocompatibility,
biodegradability,
natural support improving bioavailability towards numerous active agents.

Owing to its remarkable qualities, said protein has contributed to the production of numerous biomaterials for which the market is continuously expanding.

Among the many collagen-based preparations, the main ones seem to be as follows:
solution for cosmetics,
solution for making artificial skin,
hemostatic sponge,
healing dressings,
bone-reconstruction material,
protection capsules against active agents and improvement of their bioavailability,
biomaterials in solid or liquid form for filling flabby tissues.

When reading the foregoing list, which is in no way exhaustive, it is easy to realize that collagen is bound to become a substance of great industrial importance.

Collagen materials will be developed all that quicker as their cost price reduces.

This is the reason why the inventors have tried to use new sources of collagen with a view to implementing the industrial methods, improving yields, hence reducing the costs of preparation of the protein.

At present, the tissue mainly used for obtaining collagen is calf skin.

But two difficulties are met when using this base material.

Firstly, the skin is not, in general, removed in perfectly hygienic conditions, which implies having to use the skin as soon as possible after the animal is slaughtered.

Secondly, the skin must undergo an important treatment for removing the hairs and subcutaneous tissues. Such treatment is carried out in tanning installations implying the construction of a workshop independent from the site where the collagen is transformed into biomaterials. This type of infrastructure requires relatively high investments which will reflect on the cost of the obtained collagen.

Moreover, although calf skin is a tissue from a very young animal, it furnishes relatively small quantities of acid-soluble collagen, about 12 g of dry protein for 1 kg of fresh skin.

In order to avoid as much as possible having to treat the skin, and to improve extraction yields, the inventors have had the idea of using unpigmented fish skin.

The inventors have indeed found that pigmented fish skin is not suitable because the pigment is very difficult to eliminate during the collagen preparation process. The protein obtained in this case leads to the production of impure pigmented biomaterials.

The inventors have therefore turned their attention to fish whose skin is unpigmented and available in large quantities. The species falling in that catagory are flat fish, particularly those fished on an industrial basis such as sole, dab, turbot, brill, which are subjected to a filleting or cutting operation. The ventral skin of these fish is unpigmented, it is available, scaled, in large quantities.

SUMMARY OF THE INVENTION

Therefore, in a first aspect, the present invention relates to the use of unpigmented fish skin as novel industrial source of collagen. Preferably, said unpigmented skin is from a flat fish, particularly a ventral skin. Advantageously, said unpigmented skin is obtained after the filleting or cutting of the fresh fish and frozen immediately after filling/cutting, thus guaranteeing a very good quality of the base material, both from the bacteriological standpoint and from the standpoint of the native property of the protein.

Moreover, an unexpected advantage resides in the fact that the skin such as recovered and frozen can be used fight away for collagen extraction without any prior tanning treatments. It has also been found that the quantity of collagen extracted from said base material is about three times greater than that obtained from calf skin.

Consequently, the use of this novel source of collagen will lead to obtaining a protein of reduced cost with reproducibly preserved native properties.

In a second aspect, the present invention further relates to a method for extracting native collagen, characterized in that it uses unpigmented fish skin from which collagen is extracted.

According to a variant embodiment of this method, the unpigmented skin is the skin of a flat fish, particularly a ventral skin. Advantageously, said skin is obtained after filleting or cutting fresh fish which is frozen immediately after filleting/cutting.

Said skin is also used for extracting collagen without any prior tanning treatment.

According to a particular variant of embodiment, the skin used is unpigmented skin from flat fish fished on an industrial basis, such as for example sole, dab, turbot, brill.

According to a particular variant of embodiment, native acid-soluble collagen is extracted by extraction in an acid solution, as known to the man skilled in the art. Then, the native collagen is separated by precipitation from the supernatant, by addition of a precipitating agent, such as sodium chloride. Anyone who wishes may effect a decrosslinking of said native collagen.

The invention also relates to the native collagen obtained from unpigmented fish skin, and to any biomaterial produced totally or partially with such a collagen.

The invention will now be described with reference to an example of collagen extraction using the extraction method according to the invention, given solely by way of illustration and which could not possibly limit the scope of the invention.

EXAMPLE

Preparation of acid-soluble collagen from 40 kg of frozen sole skins

1. Grinding of the skin

The ventral skins of sole fished industrially are supplied in frozen blocks of 20 kg. These are cut into blocks of 2 kg with a band saw. The obtained pieces are then ground and defrosted with a disk mill equipped with a 40 l sealed tank. 39 kg of ground material are obtained.

2. Washing of the ground material

The ground material is washed in two successive baths of phosphate buffer (21.7 g/l NA2 HPO4 and 0.78 g/l of KH2 PO4). The ground material concentration being 1 kg for 5 l of bath and the contact time 1 hour. The ground material is separated from the buffer by centrifuging using a continuous centrifuge turning at 4000 revs/min.

The phosphate is then removed in the same conditions by two sucessive washes in deionized sterilized water.

3. Acid extraction

The ground material obtained is then placed in a 0.25M solution of acetic acid at a concentration of 1 kg for 10 l of bath. The mixture is stirred for 15 mins. and the supernatant is recovered by continuous centrifuging in the same conditions as hereinabove.

This extracting operation is carried out twice. The supernatants are collected together and the collagen that they contain is precipitated by addition of sodium chloride at a concentration of 7%. The obtained fibers are dialyzed against the deionized water until complete elimination of the salts. The obtained collagen can be either placed in acid solution again or lyophilized.

1.6 kg of dry collagen are obtained from 40 kg of fresh sole skins. The extraction yield is more than three times greater than that obtained with calf skin.

Here are the characteristics of a solution of acid-soluble collagen from sole skin in a medium at 0.1% sorbic acid.

| Chemical analyses | |
| --- | --- |
| Dry materials | 0.46 |
| Mineral materials | 0.08 |
| Total nitrogen | 0.075 |
| Total Proteins (from nitrogen) | 0.40 |
| Hydroxyproline | 0.03 |
| Collagen from hydroxyproline | 0.40 |
| Acidity (in sorbic acid) | 0.10 |
| Physical analyses | |
| Electrophoresis | |
| subunits β(200,000 daltons) 56% | |
| α(100,000 daltons) 44% | |
| no subunits less than 100,000 daltons | |
| Programmed differential scanning calorimetry: | |
| start-of-denaturation temperature in °C.: 28 | |
| end-of-denaturation temperature in °C.: 37 | |
| enthalpy of denaturation (J/mg collagen): $5 \times 10^{-2}$ | |
| X-ray diffraction | |
| presence of the helical structure. | |

The amino acid composition of the acid-soluble collagen obtained in the preceding example and which was extracted from the ventral skin of sole, has also been established.

| AMINO ACID COMPOSITION | |
| --- | --- |
| Amino acids | Number of residues for 1,000 total residues |
| Cysteic acid | 0.00 |
| Hydroxyproline | 59.58 |
| Aspartic acid | 56.74 |
| Threonine | 20.76 |
| Serine | 27.87 |
| Glutamic acid | 85.11 |
| Proline | 59.58 |
| Glycine | 326.64 |
| Alanine | 126.09 |
| Cystine | 0.00 |
| Valine | 27.59 |
| Methionine | 2.27 |
| Isoleucine | 12.68 |
| Leucine | 29.60 |
| Tyrosine | 0.00 |
| Phenylalanine | 15.47 |
| Histidine | 8.96 |
| Hydroxylysine | 4.15 |
| Lysine | 34.34 |
| Tryptophane | 0.00 |
| Arginine | 46.81 |

We claim:

1. A process for the extraction of native collagen, comprising providing a starting material consisting essentially of non-pigmented fish skin, extracting collagen from said non-pigmented fish skin, and recovering said collagen.

2. The process of claim 1, wherein said non-pigmented fish skin is a flat fish skin.

3. The process of claim 1, wherein said non-pigmented fish skin is a ventral skin of a flat fish.

4. The process of claim 2, wherein said non-pigmented fish skin is a ventral skin of a flat fish.

5. The process of claim 1, wherein said skin is obtained by cutting the skin from fresh fish and immediately freezing the skin after cutting.

6. The process of claim 1, wherein said fish is selected from the group consisting of sole, dab, turbot, and brill.

7. The process of claim 2, wherein said fish is selected from the group consisting of sole, dab, turbot, and brill.

8. The process of claim 1, comprising grinding the non-pigmented fish skin, placing the resultant ground fish skin in an acid solution to extract acid-soluble collagen, separating a supernatant containing said acid-soluble collagen, and recovering said acid-soluble collagen in native form by precipitation from said supernatant.

9. The process of claim 6, comprising grinding the non-pigmented fish skin, placing the resultant ground fish skin in an acid solution to extract acid-soluble collagen, separating a supernatant containing said acid-soluble collagen, and recovering said acid-soluble collagen in native form by precipitation from said supernatant.

10. The process of claim 8, further comprising intermediate steps after grinding said non-pigmented fish skin but prior to said acid extraction, of washing the ground skin with a phosphate buffer solution, separating said phosphate buffer solution from said ground skin, and washing the ground material with water to eliminate residual phosphate.

11. The process of claim 8, wherein said precipitation of a native collagen is performed by introducing said supernatant containing acid-soluble collagen into a sodium chloride solution to precipitate native collagen fibers.

12. The process of claim 10, wherein said precipitation of a native collagen is performed by introducing said supernatant containing acid-soluble collagen into a sodium chloride solution to precipitate native collagen fibers.

13. The process of claim 11, further comprising subjecting the resultant collagen fibers to dialysis against deionized water to eliminate salts so as to recover a native collagen essentially free of salts.

14. The process of claim 13, further comprising lyophilizing the resultant native collagen essentially free of salts.

15. The process of claim 14, wherein said native collagen has 56% of subunits $\beta$ of 200,000 dalton, 44% of subunits $\alpha$ of 100,000 dalton, and does not have subunits lower than 100,000 dalton, as measured by electrophoresis and has a helicoidal structure.

16. The process of claim 14, further comprising shaping the resultant native collagen into a biomaterial.

17. The process of claim 15, further comprising shaping the resultant native collagen into a biomaterial.

18. A process for the extraction of native collagen, comprising providing a starting material consisting essentially of non-pigmented flat fish skin, extracting collagen from said non-pigmented flat fish skin, and recovering said collagen, thereby obtaining a substantially collagen-depleted, non-pigmented fish skin, wherein said starting material is obtained by separating pigmented fish skin from non-pigmented fish skin.

* * * * *